(12) United States Patent
Shinayama et al.

(10) Patent No.: US 10,046,201 B2
(45) Date of Patent: Aug. 14, 2018

(54) ELECTRONIC APPARATUS AND PROGRAM

(71) Applicants: ASICS Corporation, Kobe-shi, Hyogo (JP); SEIKO INSTRUMENTS INC., Chiba-shi, Chiba (JP)

(72) Inventors: Ryota Shinayama, Kobe (JP); Takehiro Tagawa, Akashi (JP); Yoshinori Sugai, Chiba (JP)

(73) Assignees: ASICS CORPORATION (JP); SEIKO INSTRUMENTS INC. (JP)

( * ) Notice: Subject to any disclaimer, the term of this patent is extended or adjusted under 35 U.S.C. 154(b) by 107 days.

(21) Appl. No.: 14/902,869

(22) PCT Filed: Jul. 30, 2013

(86) PCT No.: PCT/JP2013/070587
§ 371 (c)(1),
(2) Date: Jan. 5, 2016

(87) PCT Pub. No.: WO2015/015564
PCT Pub. Date: Feb. 5, 2015

(65) Prior Publication Data
US 2016/0151673 A1 Jun. 2, 2016

(51) Int. Cl.
*A63B 24/00* (2006.01)
*G07C 1/22* (2006.01)
*G06F 19/00* (2018.01)
*G06Q 10/06* (2012.01)

(52) U.S. Cl.
CPC ...... *A63B 24/0075* (2013.01); *A63B 24/0062* (2013.01); *G06F 19/3481* (2013.01); *G06Q 10/0639* (2013.01); *G07C 1/22* (2013.01); *A63B 2024/0078* (2013.01)

(58) Field of Classification Search
None
See application file for complete search history.

(56) References Cited

U.S. PATENT DOCUMENTS

| 2008/0096726 | A1* | 4/2008 | Riley | A63B 24/0006 482/8 |
| 2008/0200312 | A1* | 8/2008 | Tagliabue | G01C 22/006 482/9 |
| 2008/0214358 | A1 | 9/2008 | Ogg et al. | 482/9 |
| 2009/0270227 | A1* | 10/2009 | Ashby | A63B 22/0023 482/8 |

(Continued)

FOREIGN PATENT DOCUMENTS

| JP | 9178869 | 7/1997 |
| JP | 2000090179 | 3/2000 |

(Continued)

OTHER PUBLICATIONS

International Search Report dated Oct. 29, 2013, issued in International Appln. No. PCT/JP2013/070587.

*Primary Examiner* — Khaja Ahmad
(74) *Attorney, Agent, or Firm* — Adams & Wilks

(57) ABSTRACT

An electronic apparatus includes: a control unit that, in an interval training in which a high intensity exercise and a low intensity exercise are repeated, calculates one or both of a high intensity exercise time for performing the high intensity exercise and a low intensity exercise time for performing the low intensity exercise based on input time information.

10 Claims, 10 Drawing Sheets

(56) References Cited

U.S. PATENT DOCUMENTS

2011/0035184 A1* 2/2011 Aaron .............. A63B 24/0006
                                                    702/158

FOREIGN PATENT DOCUMENTS

| JP | 2002028153 | 1/2002 |
| JP | 2002125957 | 5/2002 |
| JP | 2007328568 | 12/2007 |
| JP | 2007330513 | 12/2007 |
| JP | 2008229200 | 10/2008 |
| JP | 5128135    | 11/2012 |

* cited by examiner

ELECTRONIC APPARATUS AND PROGRAM

TECHNICAL FIELD

The present invention relates to an electronic apparatus and a program.

BACKGROUND

An interval training method in which high intensity training and low intensity training are alternately repeated a predetermined number of times is known as a training method. A user runs at a high speed (also referred to as a fast run) as the high intensity training and runs at a low speed (also referred to as a slow run) as the low intensity training. The distance that the user runs or the training period for which the user fast runs or slow runs is selected, for example, by a trainer based on experience.

The user performs such training by using a timer on an electronic watch that notifies the user of the training time selected by the trainer after a time elapses to thereby know that the period for which the user runs at a high speed elapses and the period for which the user runs at a jogging speed elapses.

Further, in the technology described in Patent Document 1, the heart rate of a user and which stage or level of an exercise program the user is at are determined based on a target heart rate set by the user and the heart rate measured during the training. In the technology described in Patent Document 1, it is determined whether the user needs to increase, decrease, or maintain the current heart rate, and a speech signal is output in accordance with the determination. In the technology described in Patent Document 1, a fast-paced first speech is output before the heart rate reaches a high target value or before the heart rate exceeds the high target value, then the first speech signal is stopped, and a slow-paced second speech signal is output. Note that, in the technology described in Patent Document 1, the user sets low and high target parameter values (high heart rate, low heart rate, high intensity maintaining time, and low intensity maintaining time).

RELATED ART DOCUMENTS

Patent Documents

[Patent Document 1] Japanese Patent Publication No. 5128135

SUMMARY OF INVENTION

Problem to be Solved by the Invention

However, there is a problem that in interval training, a common user cannot know for what distance and for how long the user should run at a high load or law load during training.

In view of the foregoing, an object of the present invention is to provide an electronic apparatus and a program capable of easily setting a high intensity training time and a low intensity training time in interval training.

Means for Solving the Problem

In order to achieve the above object, an electronic apparatus according to an aspect of the present invention includes: a control unit that, in an interval training in which a high intensity exercise and a low intensity exercise are repeated, calculates one or both of a high intensity exercise time for performing the high intensity exercise and a low intensity exercise time for performing the low intensity exercise based on input time information.

Further, in an electronic apparatus according to an aspect of the present invention, the control unit may use, as the time information, the best record when a user runs a predetermined distance or a time requested by the user and calculate one or both of the high intensity exercise time and the low intensity exercise time.

Further, in an electronic apparatus according to an aspect of the present invention, the control unit may calculate, based on the time information, a running level that is an index of running and may calculate the high intensity exercise time based on the calculated running level.

Further, an electronic apparatus according to an aspect of the present invention includes: a first storage unit that stores first information in which the running level is associated with the high intensity exercise time; and a second storage unit that stores second information in which the time information is associated with the low intensity exercise time, wherein the control unit may calculate the high intensity exercise time based on the calculated running level and the first information and may calculate the low intensity exercise time based on the time information and the second information.

Further, in an electronic apparatus according to an aspect of the present invention, the control unit may calculate the running level based on the time information and an input gender of the user.

Further, in an electronic apparatus according to an aspect of the present invention, the control unit may calculate the high intensity exercise time based on the running level and an input number of repetitions of the high intensity exercise and the low intensity exercise.

Further, in an electronic apparatus according to an aspect of the present invention, a relationship between the high intensity exercise time and the number of repetitions in each running level may be approximated by two or more formulas of straight lines.

Further, in an electronic apparatus according to an aspect of the present invention, the control unit may detect that a setting of the input number of repetitions is switched and may recalculate the high intensity exercise time in response to the detected result.

Further, in an electronic apparatus according to an aspect of the present invention, the control unit may detect that a setting of the input time information is switched and may recalculate the low intensity exercise time, the running level, and the high intensity exercise time in response to the detected result.

Further, in an electronic apparatus according to an aspect of the present invention, the control unit may detect that a setting of the input gender of the user is switched and may recalculate the running level and the high intensity exercise time in response to the detected result.

Further, in an electronic apparatus according to an aspect of the present invention, the electronic apparatus may be connected via a network to a terminal used by a user and include: an acquisition unit that acquires, via the network, the time information input through the terminal; and a transmission unit that transmits, to the terminal, one or both of the high intensity exercise time and the low intensity exercise time calculated by the control unit, wherein the control unit may calculate one or both of the high intensity exercise time and the low intensity exercise time based on the time information acquired by the acquisition unit.

Further, an electronic apparatus according to an aspect of the present invention may include: an input unit to which the time information is input; and a display unit that displays a result calculated by the control unit, wherein the control unit may calculate one or both of the high intensity exercise time and the low intensity exercise time based on the time information input through the input unit.

In order to achieve the above object, a program according to an aspect of the present invention is a program for causing a computer of an electronic apparatus to execute: in an interval training in which a high intensity exercise and a low intensity exercise are repeated, calculating one or both of a high intensity exercise time for performing the high intensity exercise and a low intensity exercise time for performing the low intensity exercise based on input time information.

Advantage of the Invention

According to the present invention, the electronic apparatus can easily set a high intensity training time and a low intensity training time in interval training.

DESCRIPTION OF THE EMBODIMENTS

Hereinafter, an embodiment of the present invention will be described with reference to the drawings. Further, in the following examples, an electronic watch will be described as an example of an electronic apparatus. Further, in the following examples, a training in which a user runs a track or the like will be described as an example of interval training.

First, an outline of interval training is described.

The interval training is a training in which an exercise with high load (hereinafter, referred to as a high intensity exercise) and an exercise with low load (hereinafter, referred to as a low intensity exercise) are alternately repeated a predetermined number of times. In the interval training according to the present embodiment, a user first performs a high intensity exercise for a period of time (high intensity exercise time, run time). After finishing the run time, the user performs a low intensity exercise for a period of time (low intensity exercise time, jog time).

Here, a first predetermined distance is a distance for measuring a best time as time information described below. A second predetermined distance is a target distance for performing a low intensity exercise. A third predetermined distance is a target distance for performing a high intensity exercise. Note that, the second predetermined distance and the third predetermined distance may be, for example, distances adapted to a game which the user considers as a target.

The user performs the high intensity exercise over the third predetermined distance for the period of run time and performs the low intensity exercise over the second predetermined distance for the period of jog time. Accordingly, a distance the user actually runs for the period of run time may be equal to or more than the third predetermined distance or may be equal to or less than the third predetermined distance. Similarly, a distance the user actually runs for the period of jog time may be equal to or more than the second predetermined distance or may be equal to or less than the second predetermined distance.

Figure 1:
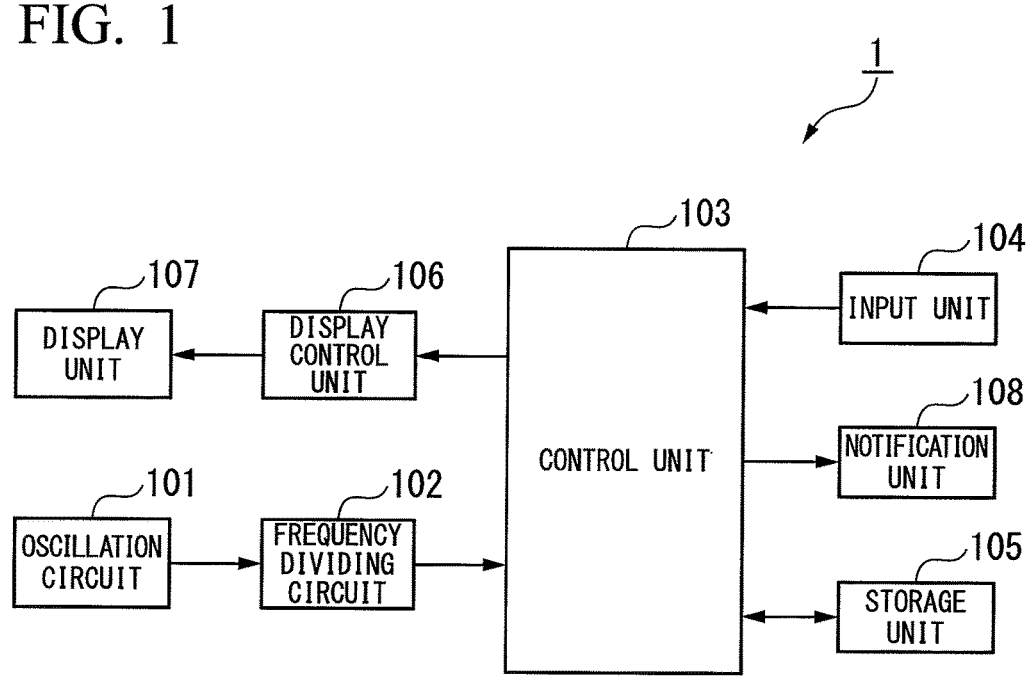
FIG. 1 is a block diagram showing a configuration of an electronic apparatus in the present embodiment.

FIG. 1 is a block diagram showing a configuration of an electronic apparatus 1 in the present embodiment. As shown in FIG. 1, the electronic apparatus 1 includes an oscillation circuit 101, a frequency dividing circuit 102, a control unit 103, an input unit 104, a storage unit 105, a display control unit 106, a display unit 107, and a notification unit 108.

Further, in the present embodiment, the electronic apparatus 1 has an operation mode of watch operation and an operation mode of interval operation. Note that, the interval operation is an operation mode in which, when the interval training is performed, a display unit 107 displays a jog time, a run time, and a training frequency.

The oscillation circuit 101 generates a reference clock signal having a predetermined frequency used for the operation of the control unit 103 and outputs the generated reference clock signal to the frequency dividing circuit 102. The predetermined frequency is, for example, 32768 Hz. Note that, the reference clock signal generated by the oscillation circuit 101 may be used in the watch operation, interval operation, and the like.

The frequency dividing circuit 102 divides the frequency of reference clock signal output by the oscillation circuit 101 and outputs a time signal that is necessary for the control unit 103 to the control unit 103.

The input unit 104 includes a button that accepts an input of a command from the user. The input unit 104 detects an input of a command from the user and outputs the detected detection result to the control unit 103 as a detection signal. The detection signal includes at least one of information indicating an operation mode, information indicating a best time, information indicating gender, and information indicating a training frequency and the start of training. Here, the best time is the current shortest time when the user runs the first predetermined distance and is a time record at a game, a time that is recorded at a practice session, and the like. Note that, the first predetermined distance is, for example, 5 km (kilometer). Further, the training frequency is the number of times of repeating alternately a fast run that is a high intensity exercise and a slow run that is a low intensity exercise.

The control unit 103 performs, depending on the detection result that is input from the input unit 104, switching of operation modes, control of each operation mode, control of each of electronic circuit elements that configure the electronic apparatus 1, and the like. Further, the control unit 103 extracts, from the detection result that is input from the input unit 104, information indicating a best time, information indicating gender, and information indicating a training frequency and causes the storage unit 105 to store the extracted information indicating a best time, information indicating gender, and information indicating a training frequency.

The control unit 103 obtains a jog time based on the information indicating a best time input from the input unit 104, and a relationship between the best time and a jog time stored in the storage unit 105. Note that, the control unit 103 may calculate the jog time based on the relationship between the best time and the jog time. Alternatively, the control unit 103 may obtain the jog time based on a relationship correspondence table between the best time and the jog time. Here, the jog time is a time for running the second predetermined distance by the slow run. The second predetermined distance is, for example, 200 m.

The control unit 103 obtains a running level based on the information indicating a best time input from the input unit 104, the information indicating gender, and a relationship between the best time and a running level stored in the storage unit 105 for each gender. Further, the control unit 103 obtains a run time based on the calculated running level, the information indicating a training frequency input from the input unit 104, and a relationship between the training frequency and a run time stored in the storage unit 105 for each running level. The control unit 103 may calculate the running level based on a relationship between the best time and the running level or may obtain the running level based on a relationship correspondence table between the best time and the running level. Further, the control unit 103 may calculate the run time based on a relationship between the training frequency and the run time for each running level or may obtain the run time based on a relationship correspondence table between the training frequency and the run time for each running level.

Note that, the run time is a time for running the third predetermined distance by the fast run. The third predetermined distance is, for example, 400 m. Further, the running level is an index that represents a level of running and, for example, represents that the run of the user is faster as the running level is higher and that the run of the user is slower as the running level is lower.

The control unit 103 outputs, to the display control unit 106 as display information, the time information of the calculated jog time and run time and the information indicating a training frequency and the rest of the training frequency. Further, the control unit 103 controls operations of a timer relating to a run time and a timer relating to a jog time in response to the information indicating the start of training included in the detection signal that is input through the input unit 104. The control unit 103 controls the notification unit 108 to report that the run time ends every time the run time elapses. Further, the control unit 103 controls the notification unit 108 to report that the jog time ends every time the jog time elapses.

Note that, the control unit 103 may read out a predetermined distance stored in the storage unit 105 when the user operates the input unit 104 and inputs a best time, and may display the predetermined distance that is read out. Alternatively, the control unit 103 may acquire a distance that is determined or changed by the operation of the input unit 104 by the user and may cause the storage unit 105 to store the acquired distance as the predetermined distance.

The display control unit 106 controls the display unit 107 to display the operation mode, the rest of the jog time, the rest of the run time, the training frequency, and the rest of the training frequency based on the display information from the control unit 103 in the interval operation.

The display unit 107 displays the operation mode, the rest of the jog time, the rest of the run time, the training frequency, the rest of the training frequency, and the like. The display unit 107 is, for example, an LCD (Liquid Crystal Display).

The storage unit 105 stores a program executed by the control unit 103, information relating to the first predetermined distance, the relationship between the best time and the jog time, the relationship between the best time and the running level for each gender, and the relationship between the training frequency and the run time for each running level. Further, the storage unit 105 stores the jog time and run time calculated by the control unit 103. Further, the storage unit 105 stores the best time, the gender, and the training frequency detected by the input unit 104. The storage unit 105 is configured, for example, by a RAM (Random Access Memory) and a ROM (Read Only Memory).

The notification unit 108 outputs a notification sound by the control of the control unit 103. The notification unit 108 is, for example, a speaker.

Figure 2A:
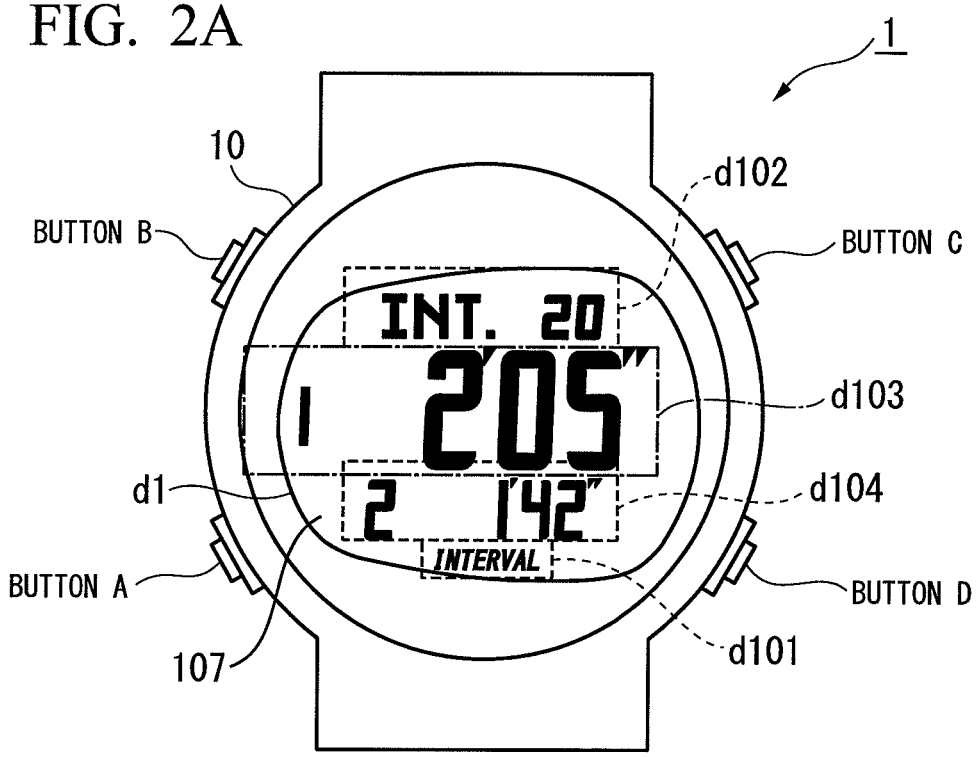
FIG. 2A is a diagram showing an example of an external form of the electronic apparatus in the present embodiment.

FIG. 2A is a diagram showing an example of an external form of the electronic apparatus 1 in the present embodiment. As shown in FIG. 2A, the electronic apparatus 1 includes a main body 10, the display unit 107, and input elements in the form of buttons A to D.

The main body 10 is a case of the electronic apparatus 1 and has a control board inside the main body 10.

The button A is, for example, a button used to start a run time timer operation and a jog time timer operation when starting training. The button B is, for example, a button used to switch between operation modes. The button C is, for example, a button used to light a backlight for a predetermined period of time. The button D is, for example, a button used to switch between displays. Note that, the example shown in FIG. 2A is an example, and the number of buttons and allocation are not limited thereto.

Figure 2B:
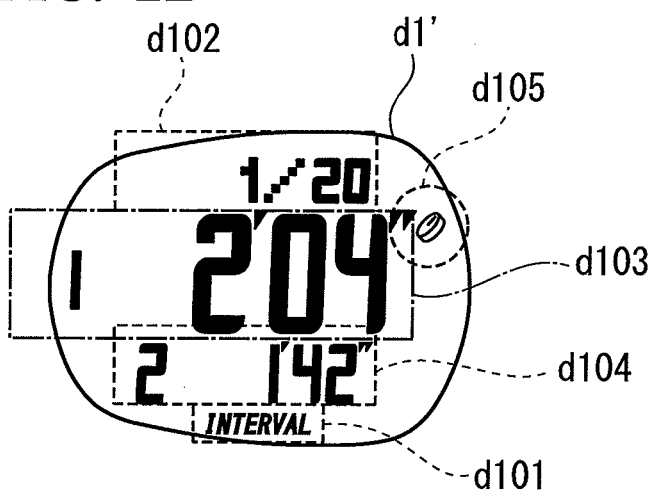
FIG. 2B is a diagram showing an example of information that is displayed on a display unit in the present embodiment.

Next, an example of information displayed on the display unit 107 in the interval operation is described using FIG. 2A and FIG. 2B. FIG. 2B is a diagram showing an example of information that is displayed on the display unit 107 in the present embodiment.

An image in a region denoted by a reference numeral d1 of FIG. 2A is an example of information displayed on the display unit 107 when a setting relating to the interval operation is completed, and the interval operation is not started. The region denoted by the reference numeral d1 includes a region d101 in which the operation mode is displayed, a region d102 in which the training frequency is displayed, a region d103 in which the run time is displayed, and a region d104 in which the jog time is displayed.

In the region d101 of FIG. 2A, "INTERVAL" indicating that the operation mode is the interval operation is displayed. In the region d102, "INT. 20" indicating that the training frequency is twenty times is displayed. In the region d103, "1" indicating that the displayed time is the run time and "2'05''" indicating that the run time is two minutes and five seconds are displayed. In the region d104, "2" indicating that the displayed time is the jog time and "1'42''" indicating that the jog time is one minute and forty two seconds are displayed.

Next, an image in a region denoted by a reference numeral d1' of FIG. 2B is an example of information displayed on the display unit 107 when the interval operation is started, and the measurement of the run time is started. The region denoted by the reference numeral d1' includes a region d105 in which an image indicating that the timer is operating is displayed in addition to the regions d101 to d104. Note that, the image displayed in the region d105 may be displayed such that the image blinks in accordance with the measurement of timer operation or may remain displayed during the time measurement. Then, the display of the image displayed in the region d105 may be erased after the measurement of the run time is finished, and the image displayed in the region d105 may be displayed at a position that corresponds to the region d104 when the measurement of the jog time is started.

Further, since the measurement of the run time is started, in the region d102, "1/20" indicating that the training is the first time of twenty times is displayed. Further, in the region d103, "1" indicating that the displayed time is the run time and "2'04''" indicating that the rest of the run time is two minutes and four seconds are displayed.

The control unit 103 causes the display unit 107 by way of the display control unit 106 to display the run time such that the run time is counted down. Then, the control unit 103 sets the display of the region d103 back to "2'05''" indicating that the displayed time is two minutes and five seconds as a calculation value of the run time while reporting that the run time is finished from the notification unit 108 when the rest of the run time becomes zero. At the same time, the control unit 103 performs control such that the timer measurement of the jog time is started. As a result, the display control unit 106 is controlled such that, during the measurement of the jog time, "2'05''" indicating that the displayed time is two minutes and five seconds as a calculation value of the run time is displayed in the region d103, and the rest of the jog time is displayed in the region d104.

Note that, FIG. 2A and FIG. 2B are an example, and the content of display, the size of each region, the arrangement of the regions, and the like are not limited thereto. For example, the positions of the region d103 and the region 104 may be upside-down. Further, the control unit 103 may display the region d103 and the region d104 to be switched during the measurement of the jog time. Further, the information displayed in the region d103 may be counted up from zero seconds to the run time. Similarly, the information displayed in the region d104 may be counted up from zero seconds to the jog time.

Next, the information stored in the storage unit 105 is described.

Figure 3:
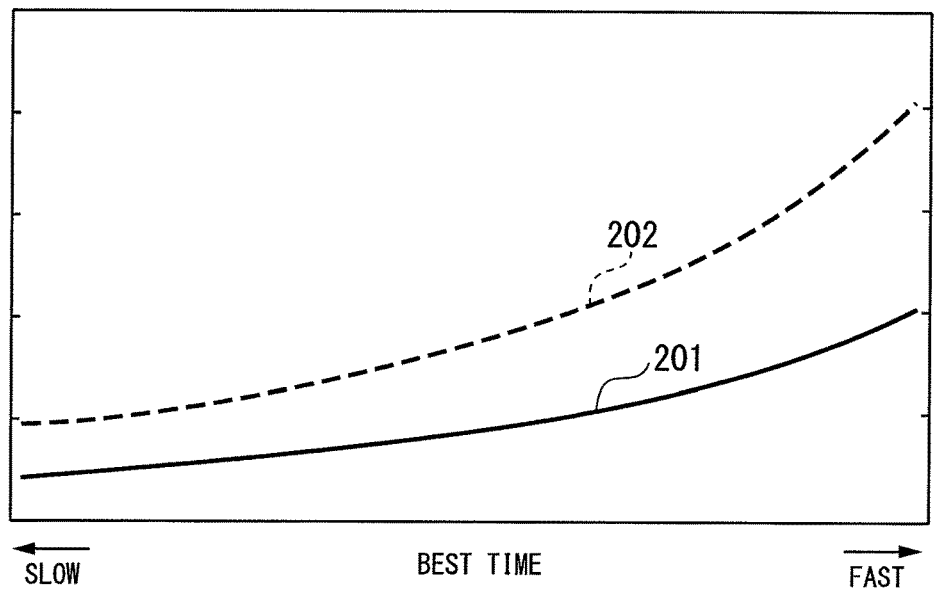
FIG. 3 is a diagram showing an example of a relationship between a best time and a running level stored in a storage unit according to the present embodiment.

FIG. 3 is a diagram showing an example of a relationship between the best time and the running level stored in the storage unit 105 according to the present embodiment. The storage unit 105 stores relationships of a curve line 201 and a curve line 202 shown in FIG. 3 in an equation or table form. In FIG. 3, the horizontal axis represents a best time, and the vertical axis represents a running level. Further, in the horizontal axis, the right direction represents that the run is fast, and the left direction represents that the run is slow. Further, in the vertical axis, the upward direction represents that the running level is high, and the downward direction represents that the running level is low.

The curve line 201 is an example of a relationship between a best time and the running level of a male. Further, the curve line 202 is an example of a relationship between a best time and a running level of female.

As represented by the curve line 201 and the curve line 202 of FIG. 3, the running level of a female is higher than the running level of a male at the same best time. Further, in an example shown in FIG. 3, as shown in the curve line 201 and the curve line 202, the gradient of a fast best time is larger than the gradient of a slow best time.

Such a relationship between the best time and the running level may be stored in the storage unit 105, for example, for each first predetermined distance.

Figure 4:
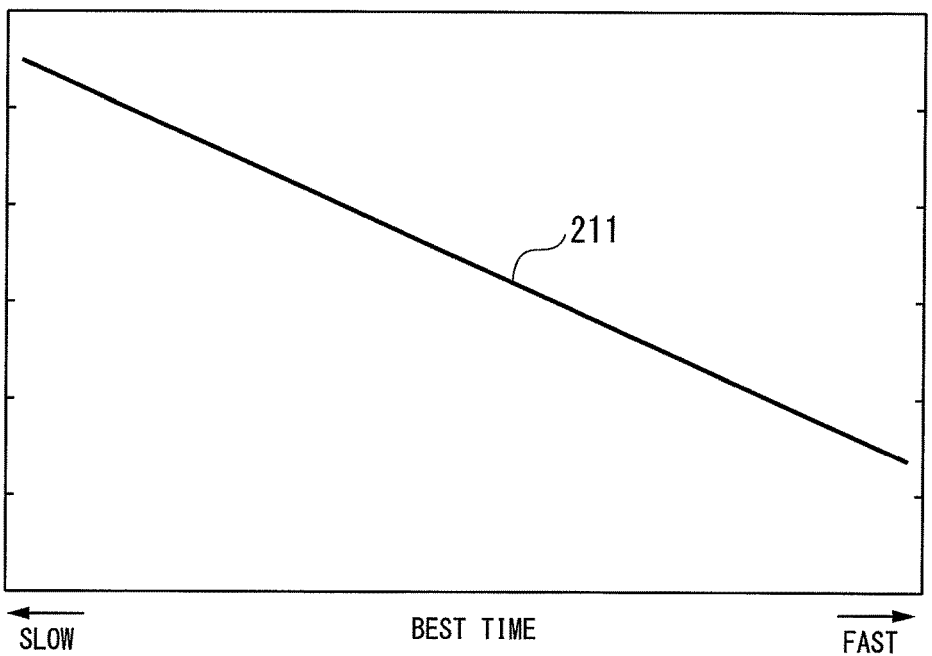
FIG. 4 is a diagram showing an example of a relationship between a best time and a jog time stored in a storage unit according to the present embodiment.

FIG. 4 is a diagram showing an example of a relationship between a best time and a jog time stored in the storage unit 105 according to the present embodiment. The storage unit 105 stores a relationship of a line 211 shown in FIG. 4 in an equation or table form. In FIG. 4, the horizontal axis represents a best time, and the vertical axis represents a jog time. Further, in the vertical axis, the upward direction represents that the jog time is slow, and the downward direction represents that the jog time is fast. As represented by the line 211 of FIG. 4, the relationship between the best time and the jog time is a relationship represented by a linear expression. Note that, the relationship between the best time and the jog time may be a relationship of polynomial expression such as a curve line, and the relationship may be approximated by one linear expression such as the line 211.

Note that, in the present embodiment, the relationship between the best time and the jog time is not different for each gender but is used for both male and female. However, the relationship between the best time and the jog time may be stored in the storage unit 105 for each gender.

Figure 5:
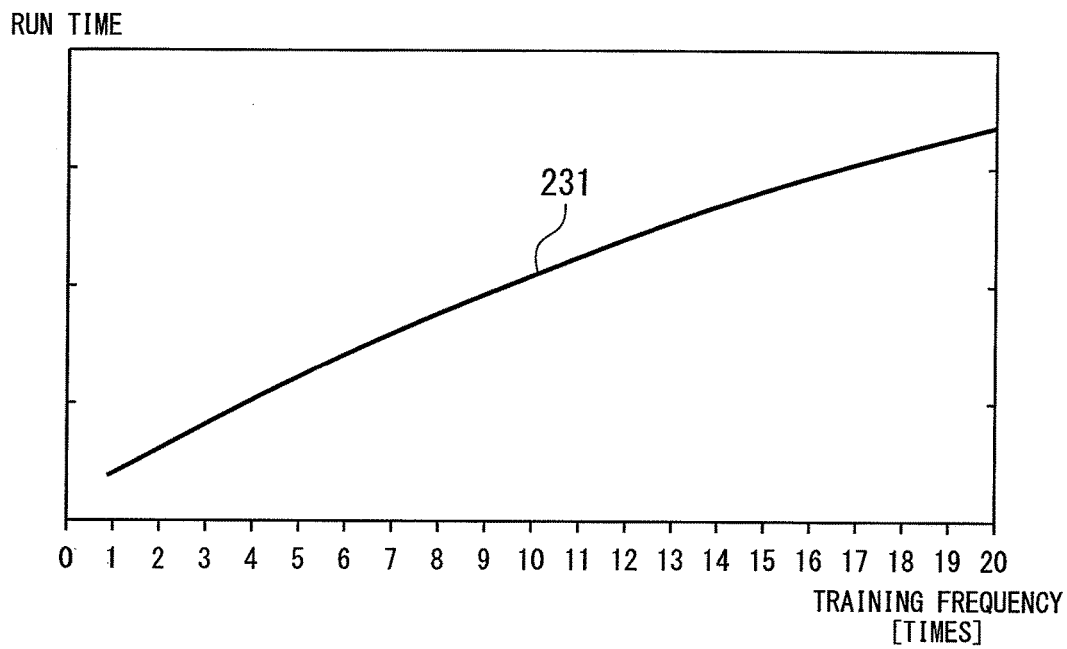
FIG. 5 is a diagram showing an example of a relationship between a training frequency and a run time according to the present embodiment.

FIG. 5 is a diagram showing an example of a relationship between a training frequency and a run time according to the present embodiment. In FIG. 5, the horizontal axis represents a training frequency, and the vertical axis represents a run time. In the vertical axis, the upward direction represents that the run time is slow, and the downward direction represents that the run time is fast.

A curve line 231 is an example of a relationship between a training frequency and a run time at a running level (n) (n represents an integer of one or more). In an example represented by the curve line 231, the run time at a small training frequency is faster than the run time at a large training frequency. Further, in an example represented by the curve line 231, the gradient is smaller as the training frequency is larger. For example, when the training frequency is close to twenty times, the control unit 103 may calculate a run time of a pace of running as a high intensity exercise the total distance in accordance with the training frequency. Further, for example, when the training frequency is close to one time, since a fast run is performed and therefore a load on the body of the user is high, the control unit 103 may calculate a run time of a pace of running as a high intensity exercise a distance that is larger than the total distance in accordance with the training frequency.

Figure 6:
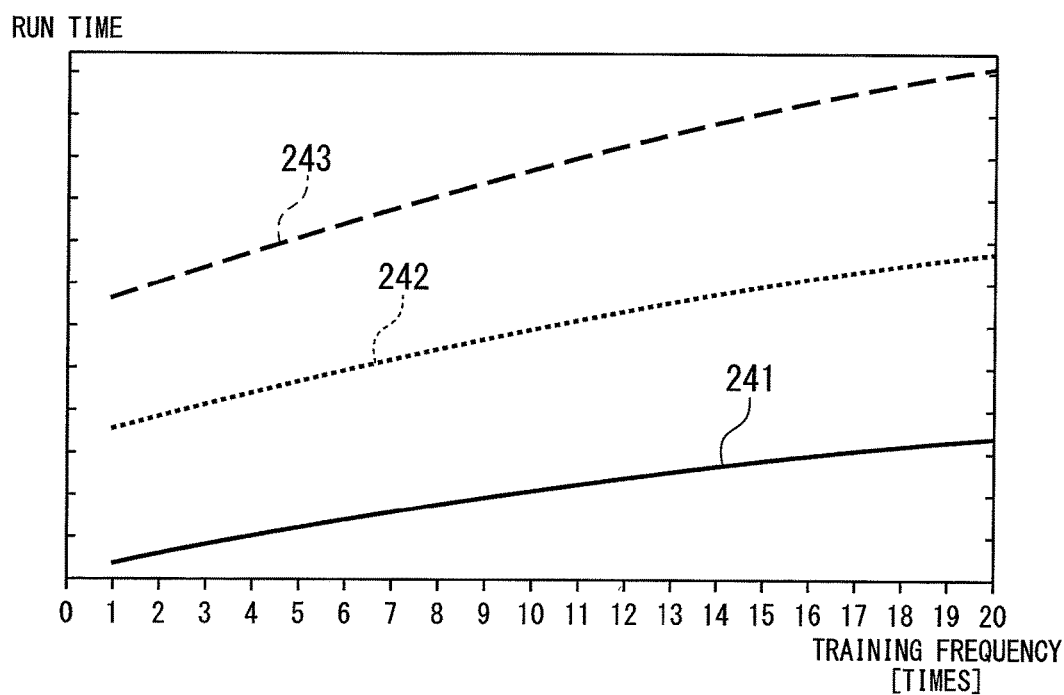
FIG. 6 is a diagram showing an example of a relationship between a training frequency and a run time stored in the storage unit according to the present embodiment.

FIG. 6 is a diagram showing an example of a relationship between a training frequency and a run time stored in the storage unit 105 according to the present embodiment. As represented by curve lines 241 to 243 of FIG. 6, the storage unit 105 stores a relationship between a training frequency and a run time for each running level. Note that, the run time of an intersection point of the horizontal axis and the vertical axis at the bottom is not zero second.

The curve lines 241 to 243 represent a relationship between a training frequency and a run time respectively at running levels (1) to (3) when the user is a male. The running level (1) is, for example, a running level of a male having a best time of running 1 km for five minutes. The running level (2) is, for example, a running level of a male having a best time of running 1 km for six minutes. Further, the running level (3) is, for example, a running level of a male having a best time of running 1 km for seven minutes. As represented by curve lines 241 to 243, in the relationships between a training frequency and a run time, the gradient of the curve line is different for each running level, and the run time is different for each training frequency. For example, the gradient of the curve line 241 of the running level (1) is smaller than the gradient of the curve line 243 of the running level (3). On the other hand, the curve line 243 of the running level (3) has a steeper gradient than the curve line 241 of the running level (1) in accordance with the increase of the training frequency. Note that, the example shown in FIG. 6 is one example, and the storage unit 105 may store three or more relationships between a training frequency and a run time for each running level.

Figure 7:
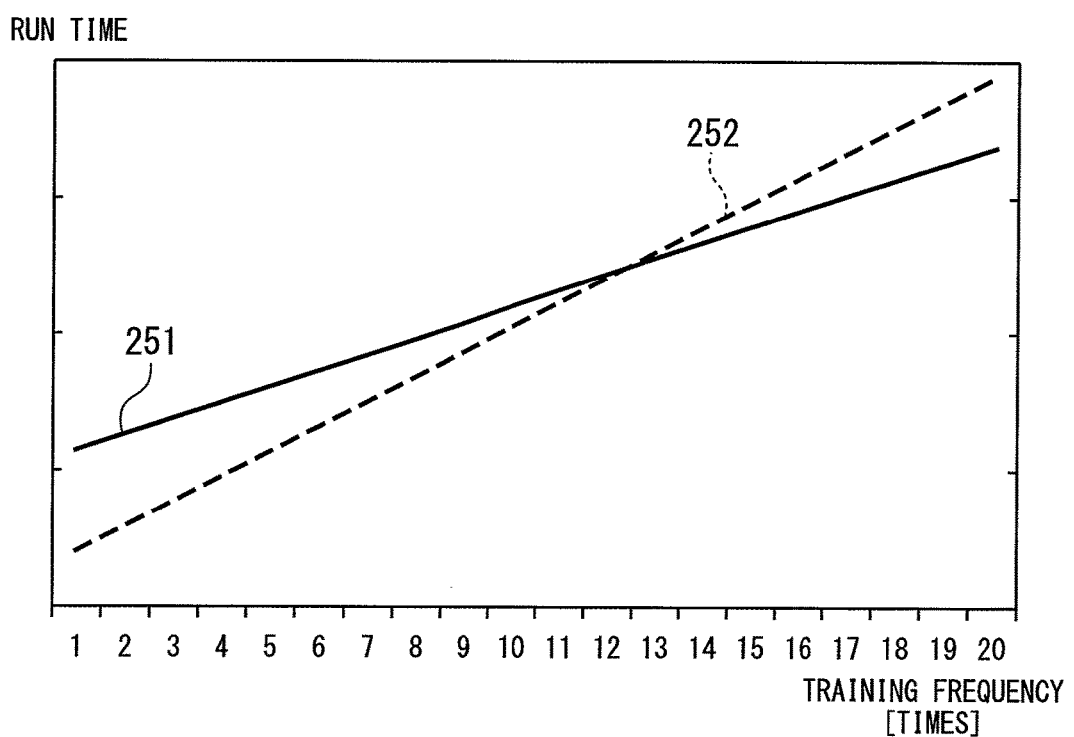
FIG. 7 is a diagram showing an example of approximating a relationship between a training frequency and a run time according to the present embodiment.

FIG. 7 is a diagram showing an example of approximating a relationship between a training frequency and a run time according to the present embodiment. In FIG. 7, an example is described in which the curve line 231 of the relationship between a training frequency and a run time of the running level (n) shown in FIG. 5 is approximated. Note that, the horizontal axis and the vertical axis are the same as, for example, those of FIG. 5. In the example shown in FIG. 7, the curve line 231 is approximated by using a straight line 251 and a straight line 252. For example, the relationship between a training frequency and a run time is represented by using the straight line 252 at a training frequency of one to twelve times and is represented by using the straight line 251 at a training frequency of thirteen to twenty times. Here, the expression of the straight line 251 is represented by $y=a_1 \cdot x + b_1$ when the run time is y and the training frequency is x. Further, the expression of the straight line 252 is represented by $y=a_2 \cdot x + b_2$. Here, $b_1$ is larger than $b_2$, and $a_1$ is smaller than $a_2$. Note that, in the example shown in FIG. 7, an example is described in which the curve line 231 is approximated by two expressions of straight lines. However, the number of straight lines is not limited thereto. There may be three or more expressions of straight lines. In this way, by approximating the relationship between a training frequency and a run time using two expressions of straight lines, the electronic apparatus 1 of the present embodiment can reduce a calculation amount of the control unit 103 and can reduce information stored in the storage unit 105.

Figure 8:
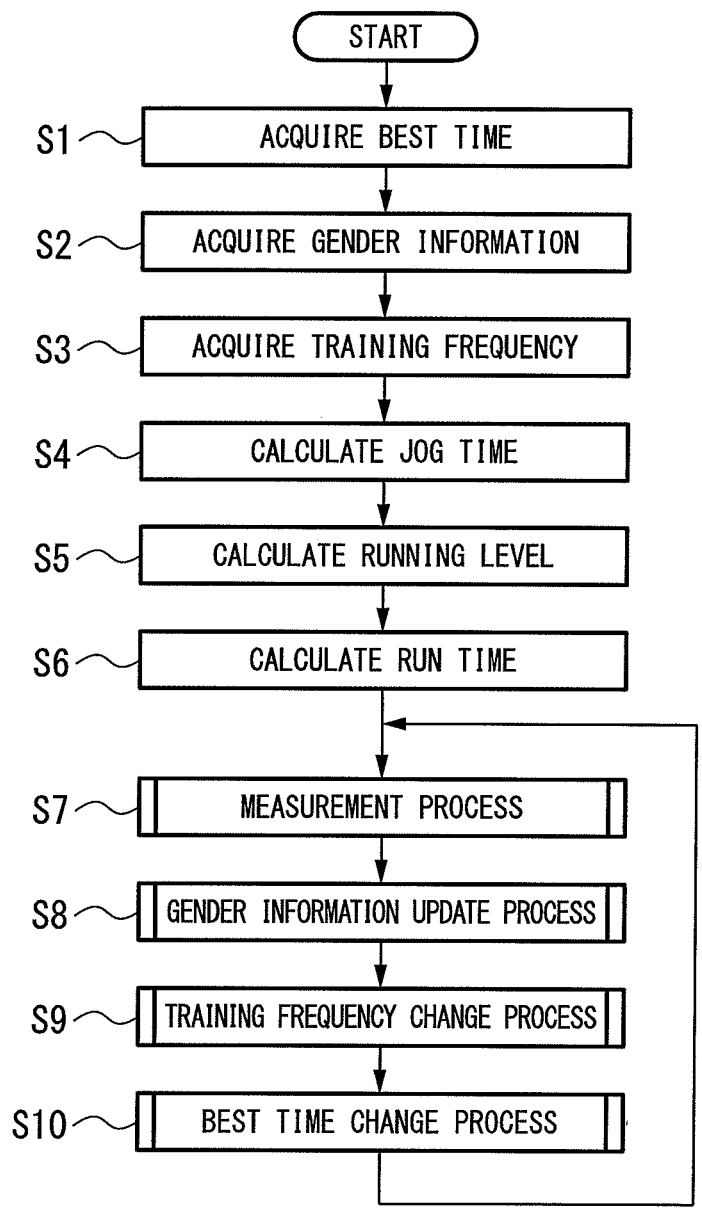
FIG. 8 is a flowchart of an example of a process sequence of interval operation according to the present embodiment.

Next, a sequence of an interval operation is described. FIG. 8 is a flowchart of an example of a process sequence of interval operation according to the present embodiment. Note that, in the following, an example is described in which the first predetermined distance is 5 km, the second predetermined distance is 200 m, and the third predetermined distance is 400 m. In such interval training, the user performs a fast run that is a high intensity exercise over about 400 m for a period of run time and performs a slow run that is a low intensity exercise over about 200 m for a period of jog time. In this way, the user alternately repeats a fast run and a slow run for the training frequency.

(Step S1) The user operates a button of the input unit 104 and inputs a best time for 5 km. The control unit 103 extracts and acquires information indicating a best time from a detection signal that is input from the input unit 104. After finishing step S1, the control unit 103 moves the process to step S2.

(Step S2) The user operates a button of the input unit 104 and inputs the gender of the user. The control unit 103 extracts and acquires information indicating gender from a detection signal that is input from the input unit 104. After finishing step S2, the control unit 103 moves the process to step S3.

(Step S3) The user operates a button of the input unit 104 and inputs a training frequency. The control unit 103 extracts and acquires information indicating a training frequency from a detection signal that is input from the input unit 104. After finishing step S3, the control unit 103 moves the process to step S4.

(Step S4) The control unit 103 calculates a jog time by using a relationship between a best time and a jog time stored in the storage unit 105 based on the best time extracted in step S1. After finishing step S4, the control unit 103 moves the process to step S5.

(Step S5) The control unit 103 calculates a running level by using a relationship between a best time and a running level stored in the storage unit 105 based on the best time extracted in step S1 and the gender extracted in step S2. After finishing step S5, the control unit 103 moves the process to step S6.

(Step S6) The control unit 103 calculates a run time by using a relationship between a training frequency and a run time stored for each running level in the storage unit 105 based on the running level calculated in step S5 and the training frequency extracted in step S3. After finishing step S6, the control unit 103 moves the process to step S7.

(Step S7) In an interval operation, the control unit 103 performs a measurement process in which a measurement of the calculated run time and jog time is repeated for the training frequency. The control unit 103 controls the display control unit 106 such that the jog time calculated in step S4, the run time calculated in step S6, the training frequency extracted in step S3, and the operation mode are displayed on the display unit 107. Note that, the measurement process is described later by using FIG. 9. After finishing step S7, the control unit 103 moves the process to step S8.

(Step S8) The control unit 103 performs a gender information update process. Note that, the gender information update process is described later by using FIG. 10. After finishing step S8, the control unit 103 moves the process to step S9.

(Step S9) The control unit 103 performs a training frequency change process. Note that, the training frequency change process is described later by using FIG. 11. After finishing step S9, the control unit 103 moves the process to step S10.

(Step S10) The control unit 103 performs a best time change process. Note that, the best time change process is described later by using FIG. 12. After finishing step S10, the control unit 103 moves the process back to step S7.

Figure 9:
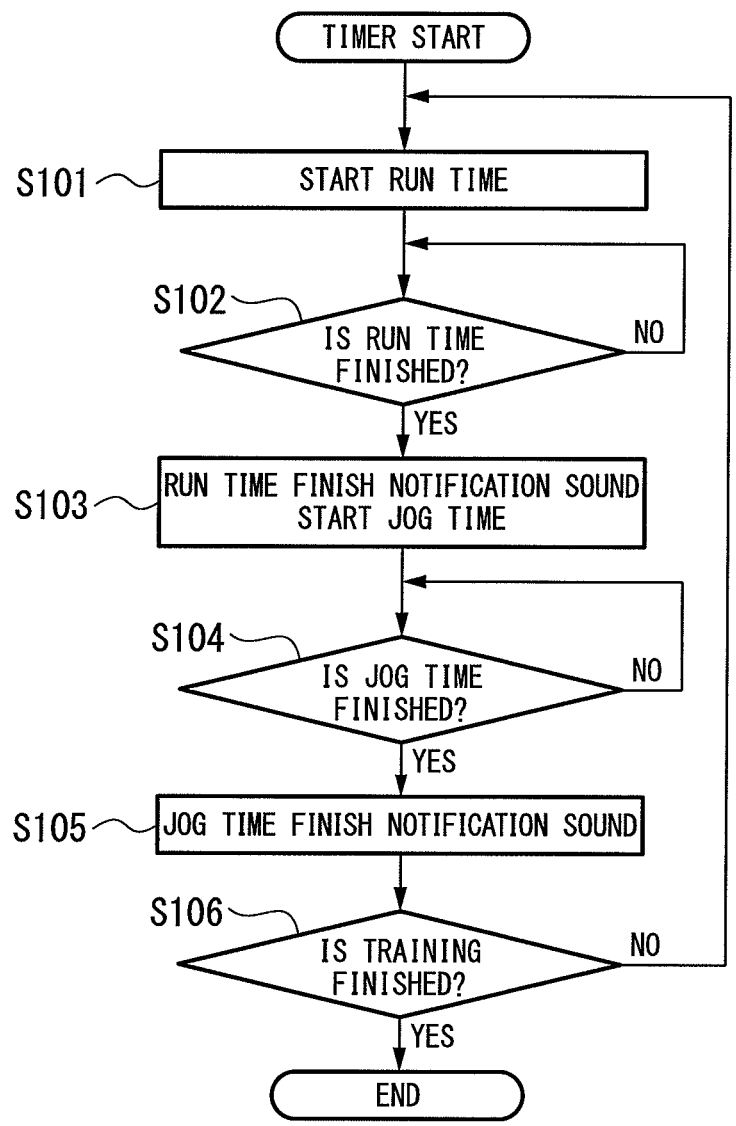
FIG. 9 is a flowchart of an example of a measurement process sequence according to the present embodiment.

Next, the measurement process is described by using FIG. 9. FIG. 9 is a flowchart of an example of a measurement process sequence according to the present embodiment.

(Step S101) The control unit 103 makes a copy of the training frequency as a value for frequency confirmation, for example, in a storage region of the storage unit 105. Next, the control unit 103 starts counting the calculated run time in accordance with the information indicating the start of training included in the detection result that is input through the input unit 104. After finishing step S101, the control unit 103 moves the process to step S102.

(Step S102) The control unit 103 determines whether or not the counting of run time is finished. The control unit 103 determines that the counting is finished when the count value becomes zero when counting down. Alternatively, the control unit 103 determines that counting is finished when the count value reaches the run time when counting up. When the control unit 103 determines that the counting of run time is finished (step S102; YES), the control unit 103 moves the process to step S103. When the control unit 103 determines that the counting of run time is not finished (step S102; NO), step S102 is repeated.

(Step S103) The control unit 103 reports that the run time is finished via the notification unit 108. The control unit 103 may start a notification by "beep" as a notification sound, for example, since three seconds before the run time is finished and may output a notification by "beep!" as a notification sound when the run time is finished. When the run time is finished, the control unit 103 resets the counter of the run time and starts counting the jog time. After finishing step S103, the control unit 103 moves the process to step S104.

(Step S104) The control unit 103 determines whether or not the counting of jog time is finished. When the control unit 103 determines that the counting of jog time is finished (step S104; YES), the control unit 103 moves the process to step S105. When the control unit 103 determines that the counting of jog time is not finished (step S104; NO), step S104 is repeated.

(Step S105) The control unit 103 reports that the jog time is finished via the notification unit 108. The control unit 103 may start a notification by "beep" as a notification sound, for example, since three seconds before the jog time is finished and may output a notification of "beep!" as a notification sound when the jog time is finished. Further, the notification sound when the jog time is finished may be different from the notification sound when the run time is finished. When the jog time is finished, the control unit 103 resets the counter of the run time. After finishing step S105, the control unit 103 moves the process to step S106.

(Step S106) The control unit 103 subtracts one from the value for frequency confirmation that is copied in the storage region of the storage unit 105 in step S101 and overwrites the value for frequency confirmation after the subtraction in the storage region to be stored. Next, the control unit 103 determines whether or not the value for frequency confirmation after the subtraction is zero or less and thereby determines whether or not the training is finished. When the control unit 103 determines that the training is finished (step S106; YES), the process is finished. When the control unit 103 determines that the training is not finished (step S106; NO), the process returns to step S101.

Then, the measurement process is finished.

Note that, in the example described above, an example is described in which a value for frequency confirmation stored in step S101 is subtracted in step S106 to determine whether or not the training is finished; however, the embodiment is not limited thereto. For example, the control unit 103 may determine whether or not the training is finished by storing zero as a value for counting in the storage unit 105 in step S101, adding one to the stored value for counting in step S106, and comparing a training frequency and the value for counting after the addition.

As described above, the electronic apparatus 1 of the present embodiment includes the control unit 103 that, in an interval training in which a high intensity exercise and a low intensity exercise are repeated, calculates at least one or both of a high intensity exercise time (run time) for performing the high intensity exercise and a low intensity exercise time (jog time) for performing the low intensity exercise based on input time information (best time).

According to the electronic apparatus 1 of this configuration, the user can use a run time and jog time suitable for the user to perform interval training only by inputting a best time, gender, and a training frequency to the electronic apparatus 1.

Note that, in the present embodiment, an example is described in which a running level is calculated based on an input best time and a run time is calculated based on the calculated running level and a training frequency; however, the embodiment is not limited thereto. The input time may be, for example, a target time that is faster than the best time or may be a standard or average time that is lower than the best time for the purpose of decreasing the exercise intensity a little. The input time can be arbitrarily set in accordance with the purpose.

The value calculated by the control unit 103 based on the running level and the training frequency may be, for example, an index representing rapidity such as a pace and a speed per 1 km. In this case, the storage unit 105 may store a relationship between a training frequency and an index representing rapidity for each running level. For example, as shown in FIG. 6, the gradients of the curve lines 241 to 243 that respectively correspond to the running levels (1) to (3) may be a gradient adapted to the index. Further, a magnitude relationship, between the gradients of the curve line 241 and the curve line 243 also may be in accordance with this index. The control unit 103 may calculate an index representing rapidity in a high intensity exercise by using a relationship between a training frequency and an index representing rapidity for each running level stored in the storage unit 105 based on the running level and the training frequency.

Similarly, the control unit 103 may calculate a rapidity index in a low intensity exercise by using a relationship between a best time and a rapidity index stored in the storage unit 105 based on the best time.

Next, a process when information input to the electronic apparatus 1 is changed is described.

Figure 10:
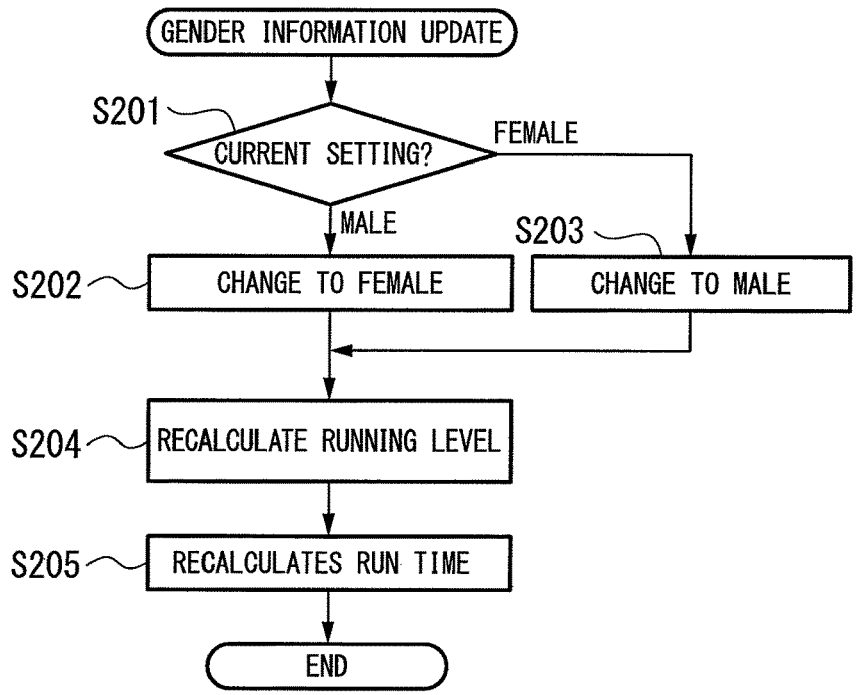
FIG. 10 is a flowchart of a process sequence of a gender information update process when gender information is changed according to the present embodiment.

First, a gender information update process when gender information is changed is described. FIG. 10 is a flowchart of a process sequence of a gender information update process when gender information is changed according to the present embodiment. Note that, the change of gender information is performed, for example, when a user is switched such as when a parent and child share one electronic apparatus 1 or when one electronic apparatus 1 is shared in club activities of a school and the like.

(Step S201) When the control unit 103 can extract a gender change command for changing the gender from a detection result input from the input unit 104, the control unit 103 starts the gender information update process. Next, the control unit 103 reads out current setting information of gender from the storage unit 105 in response to the gender change command. Next, the control unit 103 determines whether the current setting information of gender that is read out from the storage unit 105 is information indicating a male or is information indicating a female. When the control unit 103 determines that the current setting information of gender is information indicating a male (step S201; male), the process proceeds to step S202. When the control unit 103 determines that the current setting information of gender is information indicating a female (step S201; female), the process proceeds to step S203.

(Step S202) The control unit 103 changes the setting of gender stored in the storage unit 105 from a male to a female. After finishing step S202, the control unit 103 moves the process to step S204.

(Step S203) The control unit 103 changes the setting of gender stored in the storage unit 105 from a female to a male. After finishing step S203, the control unit 103 moves the process to step S204.

(Step S204) The control unit 103 recalculates a running level by using a relationship between a best time and a running level stored in the storage unit 105 based on the information indicating gender that is reset and the best time stored in the storage unit 105. After finishing step S204, the control unit 103 moves the process to step S205.

(Step S205) The control unit 103 recalculates a run time by using a relationship between a training frequency and a run time for each running level stored in the storage unit 105 based on the recalculated running level and the training frequency stored in the storage unit 105.

Then, the gender information update process is finished.

Note that, in the example shown in FIG. 10, an example is described in which the gender change command is extracted from a detection result input from the input unit 104; however, the embodiment is not limited thereto. The control unit 103 may extract information indicating gender from the detection result, compare the extracted information indicating gender and the information indicating gender stored in the storage unit 105, and, when these information do not match each other, change the information indicating gender stored in the storage unit 105. When the information indicating gender is changed in this way, the control unit 103 may perform the recalculations of step S204 and S205.

Figure 11:
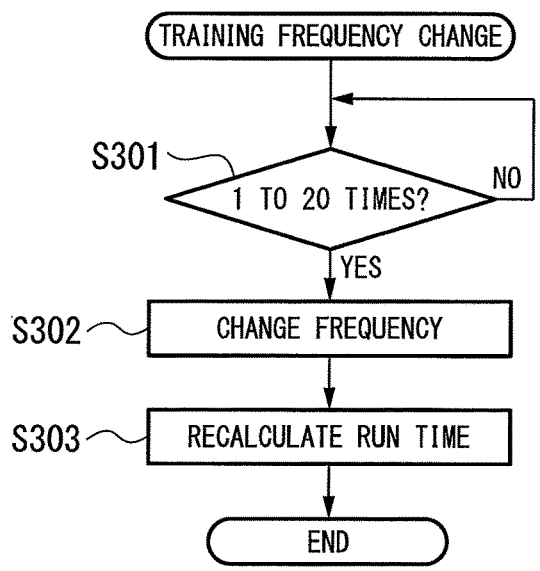
FIG. 11 is a flowchart of a process sequence of a training frequency change process when training frequency information is changed according to the present embodiment.

Next, a training frequency change process when training frequency information is changed is described. FIG. 11 is a flowchart of a process sequence of a training frequency change process when training frequency information is changed according to the present embodiment. Note that, in the following, an example in which the training frequency is set to any one of 1 to 20 times before being changed, and further, the settable training frequency in the electronic apparatus 1 is 1 to 20 times is described.

(Step S301) When the control unit 103 can extract a training frequency from a detection result input from the input unit 104, the control unit 103 starts the training frequency change process. Next, the control unit 103 determines whether or not the extracted training frequency is a value of 1 to 20. When the control unit 103 determines that the training frequency is a value of 1 to 20 (step S301; YES), the process proceeds to step S302. When the control unit 103 determines that the training frequency is not a value of 1 to 20 (step S301; NO), step S301 is repeated.

(Step S302) The control unit 103 changes the training frequency stored in the storage unit 105 to the extracted training frequency. After finishing step S302, the control unit 103 moves the process to step S303.

(Step S303) The control unit 103 recalculates a run time by using a relationship between a training frequency and a run time for each running level stored in the storage unit 105 based on the changed training frequency and the best time stored in the storage unit 105.

Then, the training frequency change process is finished.

Note that, in FIG. 11, an example in which the settable training frequency is 1 to 20 times is described; however, the embodiment is not limited thereto. The range of the settable training frequency may be one in accordance with the application such as the game for which the exercise is performed. Further, the minimum of the training frequency may be not 1 time but, for example, 5 times or the like. Similarly, the maximum of the training frequency may be not 20 times but, for example, 30 times or the like.

Figure 12:
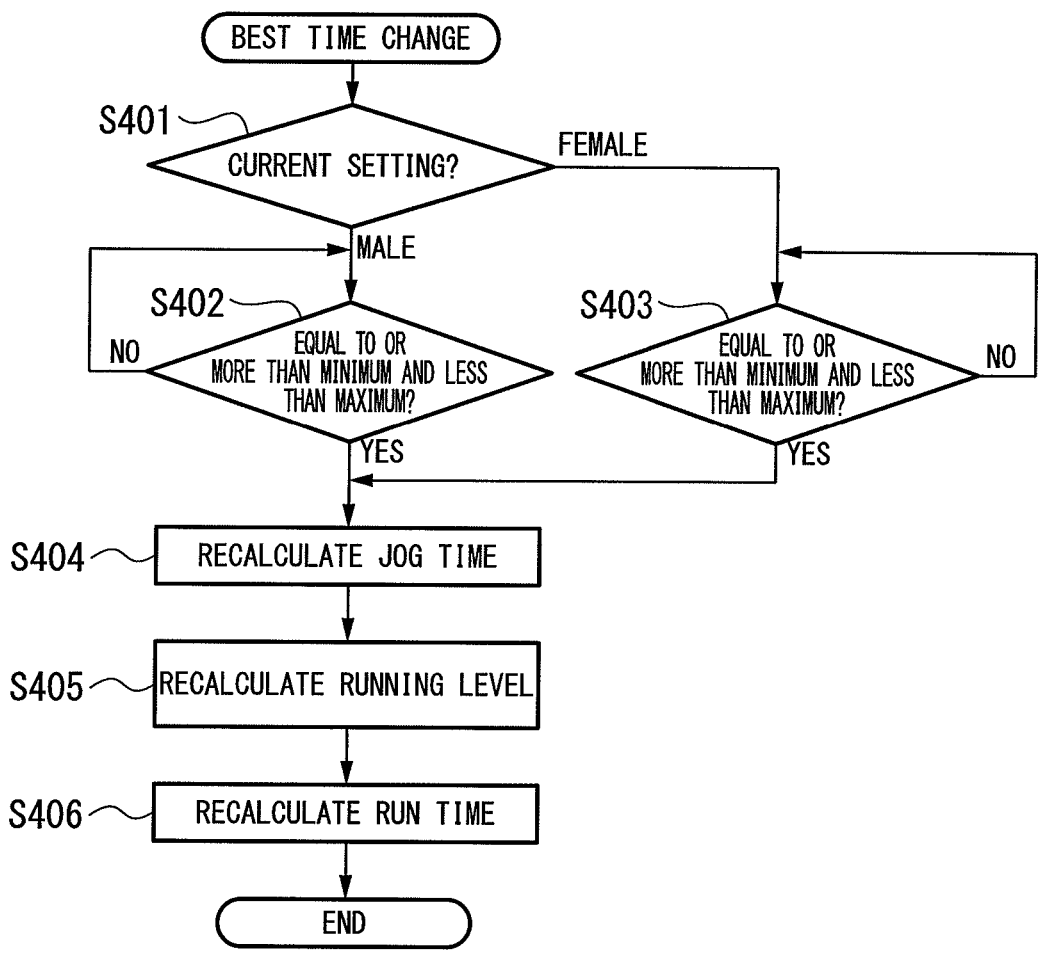
FIG. 12 is a flowchart of a process sequence of a best time change process when best time information is changed according to the present embodiment.

Next, a best time change process when best time information is changed is described. FIG. 12 is a flowchart of a process sequence of a best time change process when best time information is changed according to the present embodiment. Note that, in the example shown in FIG. 12, the storage unit 105 stores the maximum and minimum of the best time separated by gender. This maximum and minimum of the best time are, for example, values stored in advance in the storage unit 105 based on the record of a game held in the past and the like.

(Step S401) When the control unit 103 can extract a best time from a detection result input from the input unit 104, the control unit 103 starts the best time change process. Next, the control unit 103 reads out current setting information of gender from the storage unit 105 and determines whether the current setting information of gender that is read out is information indicating a male or is information indicating a female. When the control unit 103 determines that the current setting information of gender is information indicating a male (step S401; male), the process proceeds to step S402. When the control unit 103 determines that the current setting information of gender is information indicating a female (step S401; female), the process proceeds to step S403.

(Step S402) The control unit 103 reads out the minimum and maximum of the best time of a male stored in the storage unit 105. Next, the control unit 103 determines whether or not the best time extracted by the input unit 104 is equal to or more than the minimum of the best time that is read out from the storage unit 105 and is less than the maximum. When the control unit 103 determines that the extracted best time is equal to or more than the minimum of the best time that is read out and is less than the maximum (step S402; YES), the process proceeds to step S404. On the other hand, when the control unit 103 determines that the extracted best time is not equal to or more than the minimum of the best time that is read out and is not less than the maximum (step S402; NO), step S402 is repeated, and the control unit 103 waits for a re-input of a best time through the input unit 104.

(Step S403) The control unit 103 reads out the minimum and maximum of the best time of a female stored in the storage unit 105. Next, the control unit 103 determines whether or not the best time extracted by the input unit 104 is equal to or more than the minimum of the best time that is read out from the storage unit 105 and is less than the maximum. When the control unit 103 determines that the extracted best time is equal to or more than the minimum of the best time that is read out and is less than the maximum (step S403; YES), the process proceeds to step S404. On the other hand, when the control unit 103 determines that the extracted best time is not equal to or more than the minimum of the best time that is read out and is not less than the maximum (step S403; NO), step S403 is repeated, and the control unit 103 waits for a re-input of a best time through the input unit 104.

(Step S404) The control unit 103 recalculates a jog time by using a relationship between a best time and a jog time stored in the storage unit 105 based on the best time extracted by the input unit 104. After finishing step S404, the control unit 103 moves the process to step S405.

(Step S405) The control unit 103 recalculates a running level by using a relationship between a best time and a running level stored in the storage unit 105 based on the best time that is set again and the information indicating gender stored in the storage unit 105. After finishing step S405, the control unit 103 moves the process to step S406.

(Step S406) The control unit 103 recalculates a run time by using a relationship between a training frequency and a run time for each running level stored in the storage unit 105 based on the recalculated running level and the training frequency stored in the storage unit 105.

Then, the best time change process is finished.

Note that, in the present embodiment, an example is described in which, it is determined in step S402 whether or not the extracted best time is equal to or more than the minimum of the best time that is read out and is less than the maximum of the best time that is read out; however, the embodiment is not limited thereto. The control unit 103 may determine whether or not the extracted best time is equal to or more than the minimum of the best time that is read out and is equal to or less than the maximum of the best time that is read out. That is, the extracted best time may include or not include the minimum, and may include or not include the maximum. Similarly, also in step S403, the extracted best time may include or not include the minimum, and may include or not include the maximum.

As described above, according to the electronic apparatus 1 of the present embodiment, when a plurality of users share the electronic apparatus 1, even when the best time of a user is updated in a game, or even when the training frequency is changed depending on the physical condition and the like, the user may input or change only an item that the user wants to change. The electronic apparatus 1 recalculates at least one of the jog time, the running level, and the run time in accordance with the changed item. As a result, according to the electronic apparatus 1 of the present embodiment, by inputting or changing only an item that the user wants to change, the user can perform an interval training based on a jog time and a run time most suitable for the user.

Note that, in the present embodiment, a training of running a track or the like is described as an example of interval training; however, the embodiment is not limited thereto. The interval training may be, for example, a training of a walking race, a bicycle, a swimming, or the like. Therefore, when the electronic apparatus 1 is a dedicated apparatus adapted for the interval training, the relationship between the best time and the jog time stored in the storage unit 105, the relationship between the best time and the running level, and the relationship between the training frequency and the run time for each running level may be a relationship adapted for the game.

Further, when the electronic apparatus 1 is adapted for a plurality of games, a plurality of relationships between the best time and the jog time stored in the storage unit 105, a plurality of relationships between the best time and the running level, and a plurality of relationships between the training frequency and the run time for each running level may be stored in accordance with each game. In this case, the user may operate the input unit 104 to select the type of game.

Further, in the present embodiment, an example in which a user inputs to the electronic apparatus 1 the best time when the user runs the first predetermined distance the fastest is described; however, the embodiment is not limited thereto. For example, when the physical condition of the user is bad, the user may change the run time and the jog time, for example, by changing the set best time. Note that, in this case, the user inputs a time that is less than the set best time as the target time of the day, and thereby it is possible to make the load of the high intensity exercise in the run time be less than the usual exercise and to make the load of the low intensity exercise in the jog time be less than the usual exercise.

Note that, in the present embodiment, an electronic watch is described as an example of the electronic apparatus 1; however, the electronic apparatus 1 may be incorporated in an apparatus having a time measurement function. Examples of the apparatus having a time measurement function include a pedometer, a training apparatus of exercise, a measurement apparatus used for a game, a measurement instrument that measures a temporal change, a personal computer, a tablet terminal, and the like.

For example, when a personal computer has a function of the electronic apparatus 1 of the present embodiment, for example, a coach inputs a best time as time information of a player, gender, and, a training frequency to the personal computer. The personal computer may calculate a jog time and a run time by using information stored in the storage unit in the personal computer based on the input best time, gender, and training frequency for each player and may display the calculated result on a display unit of the personal computer. Note that, the information stored in the storage unit is a relationship between the best time and the jog time, a relationship between the best time and the running level, and a relationship between the training frequency and the run time for each running level. In response to a training start command from the coach, the personal computer repeats alternately counting of the run time and the counting of the jog time for the training frequency. The coach may give the player a command to perform a high intensity exercise or a command to perform a low intensity exercise based on the rest of the run time and the rest of the jog time displayed on the display unit.

Note that, when there are a plurality of players, the coach inputs a best time, gender, and a training frequency for each player to the personal computer. Then, the personal computer may calculate the jog time and the run time for each player by using information stored in the storage unit based on the input information.

Alternatively, the user may manually input the result calculated by the personal computer to the electronic watch. In this case, the personal computer may include only an operation unit 103A-1 of a control unit 103A shown in FIG. 13.

Figure 13:
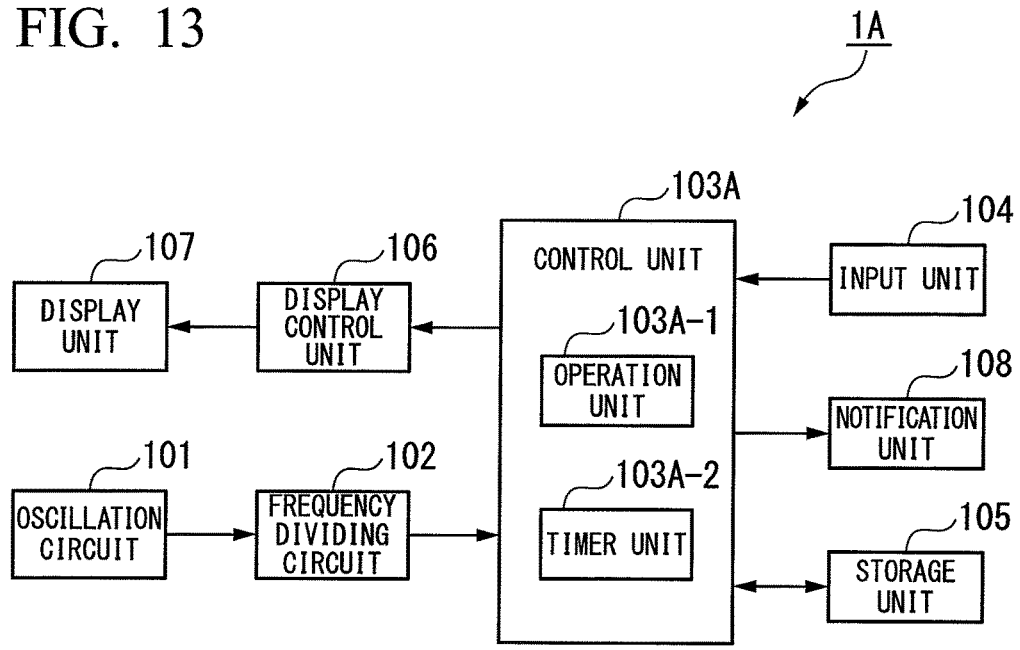
FIG. 13 is a block diagram showing a configuration of an electronic apparatus in the present embodiment.

FIG. 13 is a block diagram showing a configuration of an electronic apparatus 1A in the present embodiment. The difference between the electronic apparatus 1A shown in FIG. 13 and the electronic apparatus 1 shown in FIG. 1 is a control unit 103A. The control unit 103A includes an operation unit 103A-1 and a timer unit 103A-2.

The operation unit 103A-1 performs processes of steps S1 to S6 and S8 to S10 shown in FIG. 8. That is, the operation unit 103A-1 calculates a running level, a jog time, and a run time by using information stored in the storage unit 105 based on the acquired information. The operation unit 103A-1 outputs the calculated running level, jog time, and run time, and the acquired training frequency to the timer unit 103A-2.

The timer unit 103A-2 performs a process of step S7 shown in FIG. 8 by using the running level, jog time, run time, and training frequency input from the operation unit 103A-1. That is, the timer unit 103A-2 controls the notification unit 108 to perform a notification when the counting of run time, the counting of jog time, and the counting of run time or jog time are finished.

Figure 14:
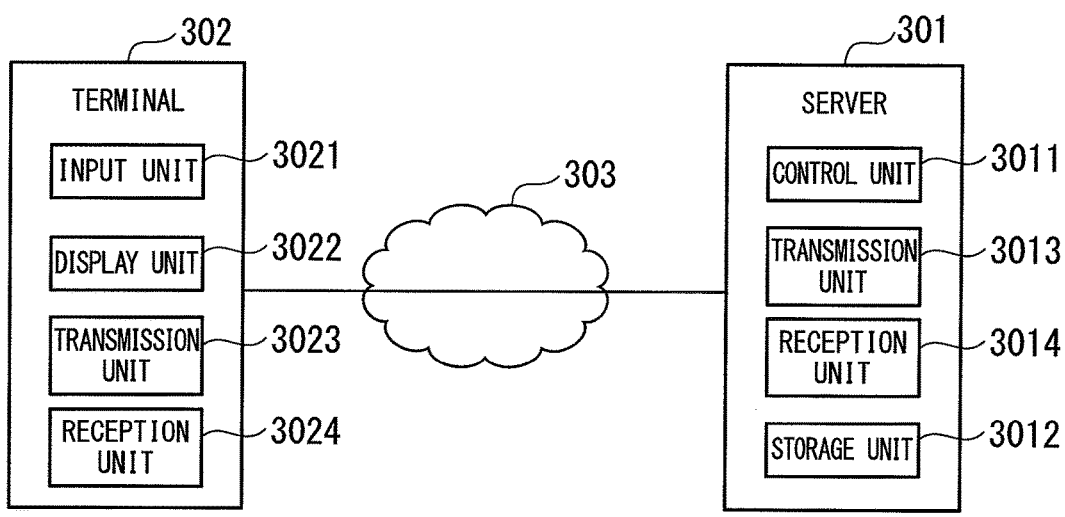
FIG. 14 is a schematic configuration diagram of an example of a system configured by a terminal and a server according to the present embodiment.

Further, the personal computer described above may be a server that is connected to a network and the like. FIG. 14 is a schematic configuration diagram of an example of a system configured by a terminal 302 and a server 301 according to the present embodiment. As shown in FIG. 14, the server 301 is connected to the terminal 302 via a network 303. The network 303 may be a wireless network or a wired network.

The terminal 302 includes an input unit 3021, a display unit 3022, a transmission unit 3023, and a reception unit 3024.

The terminal 302 is, for example, a personal computer, a tablet terminal, and the like. The terminal 302 is connected to the server 301 via the network 303.

The input unit 3021 detects information input by a user and outputs the detected input information to the transmission unit 3023. Note that, the input information is information indicating a best time, gender, or a training frequency. Note that, the input unit 3021 may be a touch panel provided on the display unit 3022.

The transmission unit 3023 transmits the information detected by the input unit 3021 to the server 301 via the network 303.

The reception unit 3024 receives, via the network 303, data of input screen that is transmitted by the server 301 and causes the display unit 3022 to display the received data of input screen. Further, the reception unit 3024 receives, via the network 303, a jog time and run time transmitted by the server 301 and causes the display unit 3022 to display the received jog time and run time.

The display unit 3022 is, for example, a liquid crystal display panel.

The server 301 includes a control unit 3011, a storage unit 3012, a transmission unit 3013, and a reception unit 3014.

The transmission unit 3013 transmits data of input screen to the terminal 302 via the network 303. Further, the transmission unit 3013 transmits the jog time and run time calculated by the control unit 3011 to the terminal 302 via the network 303.

The reception unit 3014 receives the input information transmitted from the terminal 302 via the network 303 and outputs the received input information to the control unit 3011.

The control unit 3011 calculates a running level, a jog time, and a run time by using information stored in the storage unit 3012 based on the input information received by the reception unit 3014. Note that, the control unit 3011 may calculate a running level, a jog time, and a run time for each user when the reception unit 3014 receives input information of a plurality of users. The control unit 3011 outputs the calculated jog time and run time to the transmission unit 3013.

The storage unit 3012 stores information of a relationship between a best time and a jog time, a relationship between a best time and a running level, and a relationship between a training frequency and a run time for each running level.

The user connects to the server 301 via the network 303 from the terminal 302 that the user uses and operates a keyboard included in the input unit 3021 and the like to input the best time, gender, and training frequency. Next, the control unit 3011 of the server 301 may calculate a jog time and a run time by using information stored in the storage unit 3012 based on the information received from the terminal 302. For example, the server 301 may provide these services at a dedicated site on the network. Then, the terminal 302 displays the jog time and run time received from the server 301 on the display unit 3022. The user may input the jog time and run time displayed on the display unit 3022 of the terminal 302 to the electronic apparatus 1.

As described above, the electronic apparatus (server 301) of the present embodiment is connected via the network 303 to the terminal 302 used by a user and includes an acquisition unit (reception unit 3014) that acquires, via the network, the time information input through the terminal and a transmission unit 3013 that transmits, to the terminal, one or both of the high intensity exercise time and the low intensity exercise time calculated by the control unit 3011, wherein the control unit 3011 calculates one or both of the high intensity exercise time and the low intensity exercise time based on the time information acquired by the acquisition unit.

According to this configuration, the server 301 transmits, to the terminal 302, the jog time and run time calculated by using information stored in the storage unit 3012 based on the best time, gender, and training frequency received from the terminal 302. As a result, the user inputs the best time, gender, and training frequency from the terminal 302, and thereby it is possible to confirm, on the display unit 3022 of the terminal 302, the jog time and run time that the server 301 calculates and transmits.

Further, when the personal computer and the server 301 perform a calculation of jog time and run time, a configuration may be adopted in which the user can change the first predetermined distance that corresponds to the best time while the user looks at the screen of the personal computer. In this case, the operation unit 103A-1 or the control unit 3011 may read out a relationship between a best time and a jog time, a relationship between a best time and a running level, and a relationship between a training frequency and a run time for each running level corresponding to the changed first predetermined distance, from the storage unit 105 included in the personal computer or the storage unit 3012 included in the server 301 and may calculate the running level, the run time, and the jog time. Further, a configuration may be adopted in which the user can change the upper limit of training frequency while the user looks at the screen of the personal computer.

Note that, a program for realizing the function of the electronic apparatuses 1, 1A and the server 301 in the present invention may be recorded in a computer-readable recording medium, and the program recorded in the recording medium may be read into and executed on a computer system to thereby perform the control of the electronic apparatus 1. It is assumed that the term "computer system" used herein includes an OS or hardware, such as peripherals. It is also assumed that the term "computer system" includes a WWW system which includes a homepage provision environment (or a display environment). The term "computer-readable recording medium" refers to a portable medium, such as a flexible disk, a magneto-optical disk, a ROM, or a CD-ROM, or a storage device, such as a hard disk embedded in the computer system. It is also assumed that the term "computer-readable recording medium" includes a medium which holds a program for a given time, such as a volatile memory (RAM) in the computer system which becomes a server or a client when a program is transmitted through a network, such as Internet, or a communication line, such as a telephone line.

Further, the program may be transmitted from the computer system, which stores the program in the storage device or the like, to other computer systems through a transmission medium or through transmission waves in the transmission medium. The term "transmission medium" which transmits the program refers to a medium which has a function of transmitting information like a network (communication network) such as Internet, or a communication line such as a telephone line. The program may be a program which can realize part of the above-described functions. The program may be a so-called differential file (differential program) which can realize the above-described functions by a combination with a program already recorded in the computer system.

INDUSTRIAL APPLICABILITY

The present invention is applicable to an electronic apparatus, an electronic watch, a personal computer, a server, and a program calculating a high intensity exercise time for performing a high intensity exercise and a low intensity exercise time for performing a low intensity exercise in an interval training.

DESCRIPTION OF THE REFERENCE SYMBOLS 1, 1A electronic apparatus
10 main body
A to D button
101 oscillation circuit
102 frequency dividing circuit
103, 103A, 3011 control unit
104, 3021 input unit
105, 3012 storage unit
106 display control unit
107, 3022 display unit
108 notification unit
103A-1 operation unit
103A-2 timer unit
301 server
302 terminal
303 network
3013, 3023 transmission unit
3014, 3024 reception unit

The invention claimed is:

1. An electronic apparatus comprising:
a main body;
a display unit mounted on the main body;
input elements mounted on the main body for inputting information; and
a control body disposed in the main body, the control body comprising:
a control unit which is operable in an interval training mode in which a high intensity exercise and a low intensity exercise are repeated by a user and which calculates a high intensity exercise time for performing the high intensity exercise and a low intensity exercise time for performing the low intensity exercise based on input time information which is the best time when the user performs an exercise in moving a predetermined distance or a time requested by the user;
a storage unit which includes:
a first storage unit that stores first information in which a high intensity exercise time is associated with a running level; and
a second storage unit that stores second information in which time information is associated with a low intensity exercise time; and
a notification unit,
wherein the control unit includes an operation unit and a timer unit;
wherein the operation unit is configured to:
calculate a running level, which is an index of running, based on the input time information and the first information;
calculate the high intensity exercise time, based on the calculated running level;
calculate the low intensity exercise time, based on the input time information and the second information; and
output the running level, the high intensity exercise time, and the low intensity exercise time to the timer unit, and
wherein the timer unit is configured to use the running level, the high intensity exercise time, and the low intensity exercise time to control the notification unit to output a notification sound when counting of the high intensity exercise time, counting of the low intensity exercise time, and counting of the high intensity exercise time or the low intensity exercise time are finished.

2. The electronic apparatus according to claim 1, wherein the operation unit calculates the running level based on the time information and an input gender of the user.

3. The electronic apparatus according to claim 1, wherein the operation unit calculates the high intensity exercise time based on the running level and an input number of repetitions of the high intensity exercise and the low intensity exercise.

4. The electronic apparatus according to claim 3, wherein a relationship between the high intensity exercise time and the number of repetitions in each running level is approximated by two or more formulas of straight lines.

5. The electronic apparatus according to claim 3, wherein the operation unit detects that a setting of the input number of repetitions is switched and recalculates the high intensity exercise time in response to a detected result.

6. The electronic apparatus according to claim 1, wherein the operation unit detects that a setting of the input time information is switched and recalculates the low intensity exercise time, the running level, and the high intensity exercise time in response to a detected result.

7. The electronic apparatus according to claim 2, wherein the operation unit detects that a setting of the input gender of the user is switched and recalculates the running level and the high intensity exercise time in response to the detected result.

8. The electronic apparatus according to claim 1 connected via a network to a terminal used by a user, the electronic apparatus comprising:
an acquisition unit that acquires, via the network, the time information input through the terminal; and
a transmission unit that transmits, to the terminal, one or both of the high intensity exercise time and the low intensity exercise time calculated by the operation unit, wherein
the operation unit calculates the high intensity exercise time and the low intensity exercise time based on the time information acquired by the acquisition unit.

9. The electronic apparatus according to claim 1, comprising:
an input unit including the input elements for inputting the time information,
wherein the display unit displays a result calculated by the operation unit, and wherein the operation unit calculates the high intensity exercise time and the low intensity exercise time based on the time information input through the input unit.

10. An electronic apparatus comprising:
a main body;
a display unit mounted on the main body;
input elements mounted on the main body for inputting information; and
a control body disposed in the main body, the control body including a computer and a program for causing the computer to execute:
a step of calculating, in an interval training mode in which a high intensity exercise and a low intensity exercise are repeated, one or both of a high intensity exercise time for performing the high intensity exercise and a low intensity exercise time for performing the low intensity exercise based on input time information, which is the best time when a user performs an exercise in moving a predetermined distance or a time requested by the user,
wherein the step of calculating includes:
 calculating a running level, which is an index of running, based on the input time information and first information stored in which a high intensity exercise time is associated with a running level;
 calculating the high intensity exercise time, based on the calculated running level; and
 calculating the low intensity exercise time, based on the input time information and second information stored in which time information is associated with a low intensity exercise time;
a step of outputting the running level, the high intensity exercise time, and the low intensity exercise time to a timer unit; and
a step of controlling the timer unit to use the running level, the high intensity exercise time, and the low intensity exercise time to control a notification unit to output a notification sound when counting of the high intensity exercise time, counting of the low intensity exercise time, and counting of the high intensity exercise time or the low intensity exercise time are finished.

\* \* \* \* \*